(12) United States Patent
Remmerswaal et al.

(10) Patent No.: US 9,072,432 B2
(45) Date of Patent: Jul. 7, 2015

(54) BRONCHOSCOPIC MANIFOLD

(75) Inventors: Johannes Franciscus Marinus Remmerswaal, Delft (NL); Elinard Wilco Theuvenet, Delft (DE)

(73) Assignee: TELEFLEX MEDICAL EUROPE LTD., Athlone Westmeath (IE)

( * ) Notice: Subject to any disclaimer, the term of this patent is extended or adjusted under 35 U.S.C. 154(b) by 314 days.

(21) Appl. No.: 13/256,296

(22) PCT Filed: Mar. 12, 2010

(86) PCT No.: PCT/NL2010/050132
§ 371 (c)(1),
(2), (4) Date: Nov. 30, 2011

(87) PCT Pub. No.: WO2010/104393
PCT Pub. Date: Sep. 16, 2010

(65) Prior Publication Data
US 2012/0123208 A1    May 17, 2012

(30) Foreign Application Priority Data
Mar. 13, 2009   (NL) ...................................... 2002622

(51) Int. Cl.
*A61M 16/08*   (2006.01)
*A61B 1/018*   (2006.01)
*A61B 1/267*   (2006.01)
*A61B 5/06*    (2006.01)

(52) U.S. Cl.
CPC ............ *A61B 1/018* (2013.01); *A61M 16/0875* (2013.01); *A61M 16/0833* (2013.01); *A61B 1/267* (2013.01); *A61B 5/064* (2013.01)

(58) Field of Classification Search
CPC ..................... A61M 16/0875; A61M 16/0816;
A61M 16/0833; A61M 16/04; A61B 1/00112;
A61B 1/00119; A61B 1/00121; A61B 1/018;
A61B 1/012; A61B 1/267; A61B 1/2676
USPC .................. 128/200.26, 207.14–207.17, 912;
600/114
See application file for complete search history.

(56) References Cited

U.S. PATENT DOCUMENTS

| | | | |
|---|---|---|---|
| 3,630,547 A |   | 12/1971 | Hartshorn, Jr. |
| 4,240,417 A | * | 12/1980 | Holever .................... 128/203.12 |
| 4,580,556 A | * | 4/1986  | Kondur ..................... 128/206.28 |
| 5,065,754 A | * | 11/1991 | Jensen ...................... 128/200.26 |
| 5,309,906 A | * | 5/1994  | LaBombard .............. 128/207.14 |
| 5,368,017 A | * | 11/1994 | Sorenson et al. ......... 128/200.26 |

(Continued)

FOREIGN PATENT DOCUMENTS

| | | |
|---|---|---|
| JP | 2002-113101 | 4/2002 |
| SU | 1 621 945 A1 | 1/1991 |

(Continued)

OTHER PUBLICATIONS

International Search Report, dated Jun. 17, 2010, from corresponding PCT application.

*Primary Examiner* — Valerie L Skorupa
(74) *Attorney, Agent, or Firm* — Baker & Hostetler LLP

(57) ABSTRACT

A multi-port manifold includes an instrument port, bronchoscope inlet, entrance for air and common exit. It is proposed to position the instrument port in line with the exit. The bronchoscope inlet is positioned at a very small angle with respect to the instrument port, while the air entrance extends at right angles to the plane defined by the axes of the port and the inlet.

19 Claims, 5 Drawing Sheets

(56) References Cited

U.S. PATENT DOCUMENTS

| | | | |
|---|---|---|---|
| 5,775,325 A * | 7/1998 | Russo | 128/205.12 |
| 6,086,529 A * | 7/2000 | Arndt | 600/114 |
| 6,520,183 B2 * | 2/2003 | Amar | 128/207.14 |
| 6,615,835 B1 * | 9/2003 | Cise et al. | 128/207.14 |
| 7,036,509 B2 * | 5/2006 | Rapacki et al. | 128/207.14 |
| 7,473,219 B1 * | 1/2009 | Glenn | 600/114 |
| 2003/0042736 A1 | 3/2003 | Vila | |
| 2005/0161048 A1 | 7/2005 | Rapacki et al. | |
| 2008/0190434 A1 | 8/2008 | Tjong Joe Wai | |
| 2010/0147310 A1 * | 6/2010 | Brewer et al. | 128/207.14 |

FOREIGN PATENT DOCUMENTS

| | | |
|---|---|---|
| WO | 00/56385 A1 | 9/2000 |
| WO | 2005/042079 A1 | 5/2005 |

* cited by examiner

BRONCHOSCOPIC MANIFOLD

The present invention relates to a bronchoscopic manifold according to the preamble of claim 1.

A manifold of this type is generally known from the prior art and is used when investigating and performing actions on lungs, in particular involving humans. U.S. Pat. No. 6,086,529 discloses an example of such a bronchoscopic manifold, in which a bronchoscope is introduced via the instrument port and the gas exit, which are in line with one another. The stub extending laterally therefrom is used for the introduction of a further instrument. The instrument port and bronchoscope inlet define a plane and this plane also comprises the gas input.

U.S. Pat. No. 7,473,219 discloses a similar bronchoscopic manifold. U.S. Pat. No. 6,615,835 B1 describes a branched bronchoscopic manifold in which the bronchoscope inlet and instrument port are formed as a single part which is clamped onto a further part which consists of gas entrance and gas exit. The part which consists of the instrument port and the bronchoscope inlet is of a design which is so flexible that by simply tilting, either the instrument port or the bronchoscope inlet comes to lie in line with the gas exit. In all positions, the gas entrance here remains situated in the plane defined by the gas entrance and the instrument port.

It is an object of the present invention to provide an improved manifold which makes it possible to optimize the manoeuvring of the various instruments, even when the space is restricted.

In addition, it is an object of the present invention to facilitate connection of the various instruments and/or hoses to the device. A further object of the present invention is to produce a compact manifold design.

In addition, it is a further object of the present invention to prevent damage and wear on the instruments and/or catheters used resulting from bending as much as possible and to make it possible to improve positioning of the instruments and/or catheters used.

The term bronchoscopic manifold is understood as referring to a manifold which is used when performing operations on or when diagnosing the condition of airways of human patients. In this case, the passages used, such as the gas exit, gas entrance, instrument port and bronchoscope inlet, have an internal diameter ranging from 6 to 16 mm.

These and further objects are achieved by means of a bronchoscopic manifold which can be fitted to a respiration tube and has the features of claim 1.

By bringing the exit and the instrument entrance in line according to the invention, a bend which is present in the manifold does not cause any impediment when manoeuvring the instrument. This is particularly important if the correct position of the free end of the instrument which is situated inside the airways is of importance. This position is understood to refer to both the rotational position and the distance to the manifold.

An example of an instrument where the position is very important is a so-called blocker. A blocker is a catheter which is provided with one or two inflatable balloons at its free end to block one or both bronchi. In particular if the instrument is embodied to block either one or both bronchi at their branching, it is very important that the two parts branching off from the line and provided with a balloon are situated in the correct rotational position with respect to the patient in question.

According to the invention, the axis of the inlet and the axis of the port defines a plane, with the axis of the entrance extending at an angle with respect to the plane. This angle is preferably −45° with respect to the perpendicular of the plane to +45° with respect to the perpendicular of the plane and is more particularly substantially at right angles to the plane.

As a result thereof, the separation of the connections can be improved, which greatly facilitates manoeuvring. In addition, the hose for the supply of air can be arranged in a simple position, preferably at right angles to the patient's chest plane. In addition, staff can be situated on either side of the patient during treatment in order to perform actions such as connecting to the air hose and/or entrance and/or artificial respiration. In addition, problems with connections can be prevented, in particular in the case of operations where the patient is lying on his or her back.

According to a particular embodiment of the present invention, the angle between the port and the inlet, that is to say the angle between the respective axes thereof, is relatively small. More particularly, it is smaller than 15°. According to the present invention, this angle can be reduced to such an extent that the peripheral edges of the free ends of the port and inlet are partially shared. This means that, in top view, the free ends of the port and the inlet comprise two openings which are directly adjacent to one another and have a common partition.

According to a further embodiment of the present invention, the port is provided with a closure at its free end, as is the inlet. This closure may be threaded and may be in the form of a plug or of a pierceable diaphragm. According to a particular embodiment of the present invention, the port for the catheter is provided with a closure which is configured as a bellows and has a central inlet opening. According to a further advantageous embodiment, the closures of the inlet and the port are connected to one another, thus reducing the risk of lose parts ending up in a patient.

According to a further particular embodiment of the invention, the entrance for the supply of air is arranged in such a manner that if, seen from the point of view of an observer at right angles to the plane of the axes of the port and the inlet, the free end of the inlet is situated to the right of the free end of the port and the exit is situated below, the entrance extends towards the user.

According to the invention, the port and inlet can be present in both the body of the adapter and in a closure which may be positioned thereon.

According to a particular embodiment of the invention, the bronchoscopic manifold solely comprises a gas entrance, instrument port, bronchoscope inlet and a single exit.

According to a further particular embodiment of the present invention, however, the body of the adapter comprises a single duct which is shared by the port and inlet and the free end of this duct is provided with a closure, with this port and inlet being defined while being situated at a distance from one another in this closure. Thus, a particularly small mutual angle can be achieved for introducing, for example, a bronchoscope and the respective instrument, such as a blocker, resulting in the instruments used only being curved to a minimal degree. Using this construction, it is possible to keep the angle of curvature of for example a bronchoscope in the adapter as small as possible, thus limiting damage as much as possible.

If the angle between the instrument port and the bronchoscope inlet is relatively small and one of the two comprises a threaded closure, it is preferable for the part which is threaded to extend substantially further than the other of either the instrument port or the bronchoscope inlet in order thus to facilitate the manoeuvring of the part which is to be screwed on.

The invention also relates to an assembly comprising a manifold as described above and a device blocking an airway, which device comprises a line provided with a sealing balloon which is arranged at the introduction end, with this device being arranged in this port. More particularly, a marking is provided on this device (blocker), which marking may comprise both the depth and the rotational position. In addition, a colour code or symbol code may be used. According to the present invention, this airway-blocking device is preferably introduced via the instrument port, that is to say the port which is situated in line with the gas exit.

The blocker may also be forked with a balloon being provided on each fork end for closing off each of the air pipes near the carina. In particular for small children, the balloon may be replaced by a non-inflatable part.

The above-described colour code or other code, such as a profiling or the use of symbols may be the same for a balloon and the associated operating part. Thus, the treating surgeon situated next to the patient can accurately determine the position of each of the two balloons with the aid of the operating part. In the case of the embodiment comprising a balloon, it is possible to determine in which airway it is situated. Using the depth marking, the treating physician can clearly see how far inside the airways the balloon is situated and how far it can be moved out of the airways. This applies in particular to the area near the carina.

It should be understood that this forked variant, in which two balloons are preferably used and in which the above-described coding can be used, can also be embodied to work independently of the above-described adapter, i.e. the particular embodiment of the adapter, so that it can be used in combination with any other kind of adapter.

According to a further embodiment of the present invention, a combination of an adapter and an airway-blocking device is provided, which airway-blocking device comprises a line provided with two balloons embodied to be introduced into each of the bronchi. Therein a closure has to be present between the adapter and the line of the airway-blocking device and, according to the present invention, this is embodied such that axial movement of the line of the airway-blocking device with respect to the adapter is possible. As a result thereof, it is possible to allow mutual displacement of the lungs and the adapter while performing surgical and diagnostic actions on the lungs without the risk of the balloon being moved out of its desired position in the bronchus.

It will be understood that this combination can be provided with any kind of adapter. However, it is preferred if the combination is used together with the above-described adapter.

The above-described and further details of the present invention will become clear from the attached drawings which illustrate a preferred embodiment, in which:

FIG. 1 diagrammatically shows a front view of a manifold according to the present invention;

FIG. 2 shows a perspective view of the manifold according to the present invention;

FIG. 3 diagrammatically shows the different possible positions of axis 10 of part 5;

Figure 1:
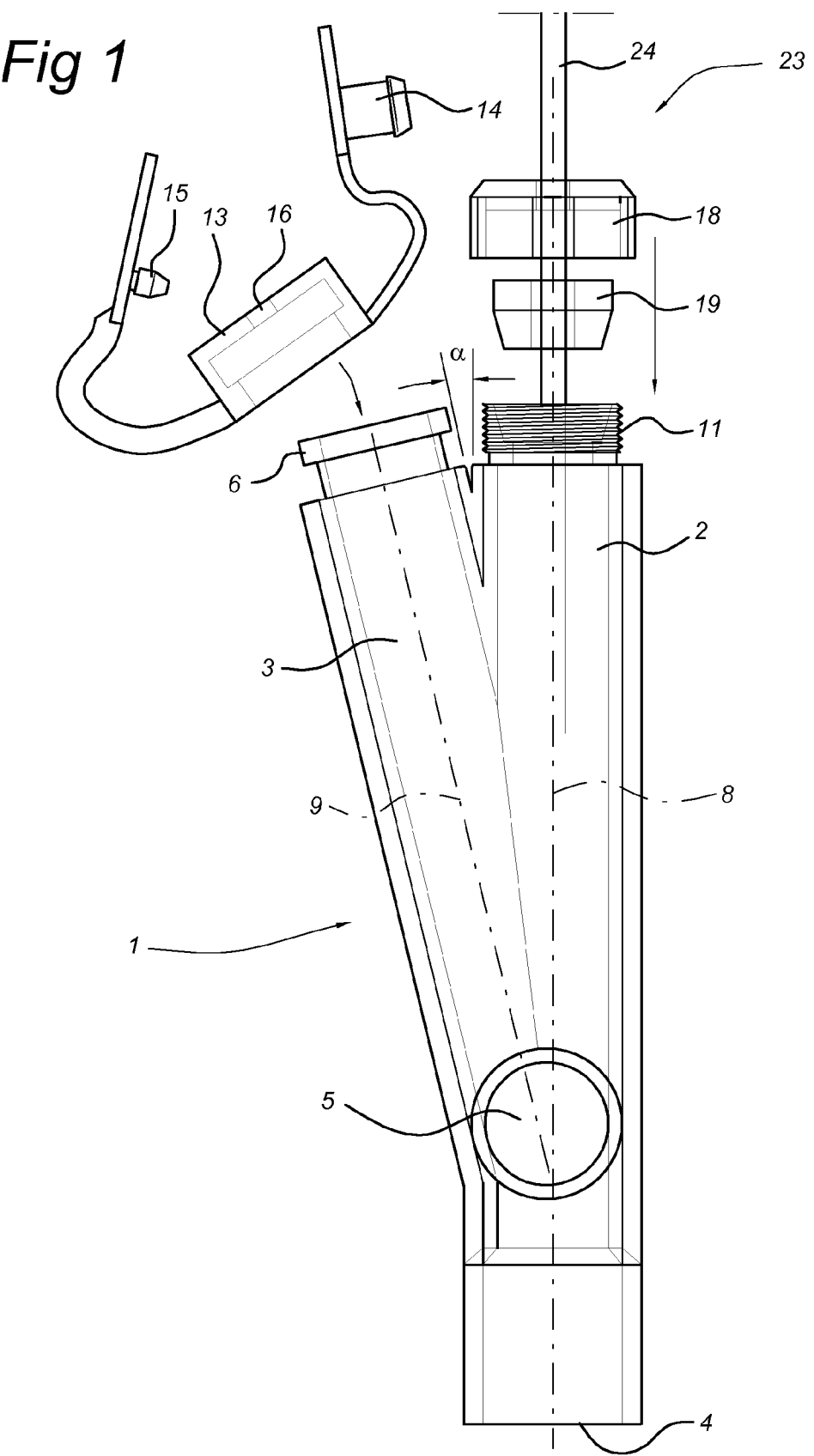

In the figures, the manifold or multi-port adapter is designated overall by reference numeral 1 and consists of a (transparent) plastic part or body. Adapter 1 is provided with an (instrument) port 2, a (bronchoscope) inlet 3 and an entrance 5 illustrated in FIG. 1 for a treatment gas such as air. Reference numeral 4 designates the exit which is shared by these various parts.

The figures show that the axis 9 of the inlet 3 and the axis 8 of the port 2 enclose a relatively small angle α. According to the invention, this angle is smaller than 15° and more particularly is approximately 10°.

Figure 2:
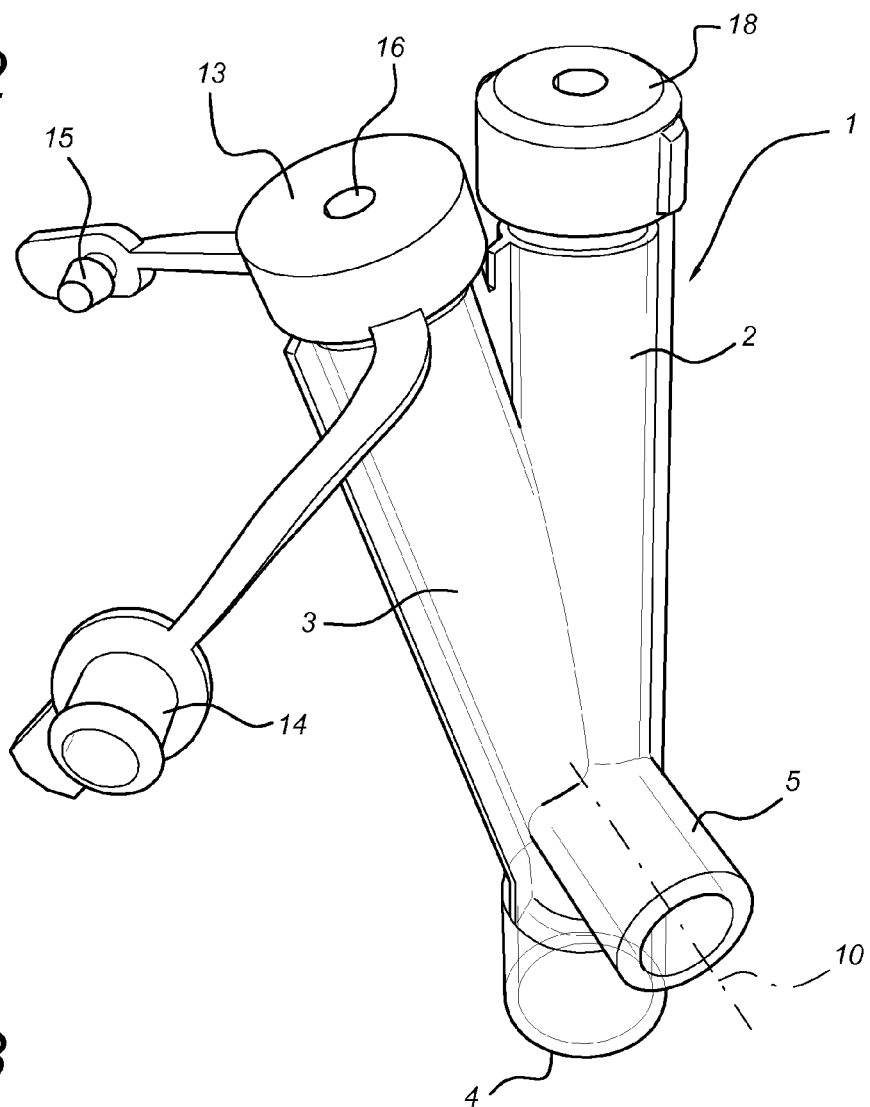

In addition, the two axes 8 and 9 define a plane. According to the present invention, the entrance 5, and more particularly its axis 10 (FIG. 2), extends at right angles to this plane. Both the port 2 and the inlet 3 may be provided with a closure. According to the present invention, the inlet 3 is provided with a click-fit edge 6 over which a cap 13 comprising an opening 16 which can be closed by an ancillary plug 15 can be attached. A bronchoscope can be introduced into this opening in a sealing manner.

Figure 3:
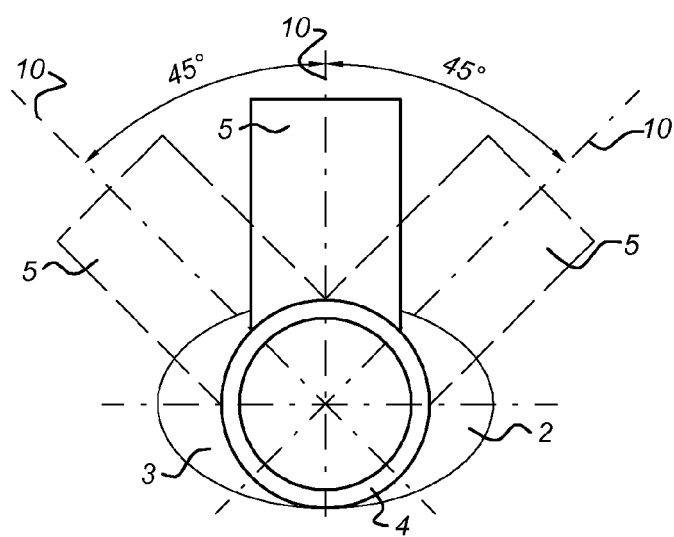

FIG. 3 diagrammatically shows the different positions of axis 10. It can be seen that deviations at an angle of +45° or −45° are possible with respect to the perpendicular position illustrated in FIG. 2.

The port 2 can also be closed using a sealing cap 14. To this end, this cap 14 is pushed into the interior of port 2, which port 2 is provided with screw thread 11 at its free end.

With the use which is to be described below, the sealing cap 14 will be removed and, for example, a blocker 23 which is to be described with reference to FIG. 4 will be introduced. This blocker 23 has a conduit 24 which comes already fitted with a gasket denoted by reference numeral 19 and with a screw cap denoted by reference numeral 18. The screw thread of screw cap 18 corresponds to that of the screw thread 11, so that a clamping fitting is possible.

The position of entrance 5 with respect to the port and inlet is preferably as is illustrated in the figures. However, it is also possible for the entrance to extend away from the observer instead of towards the observer.

Figure 4:
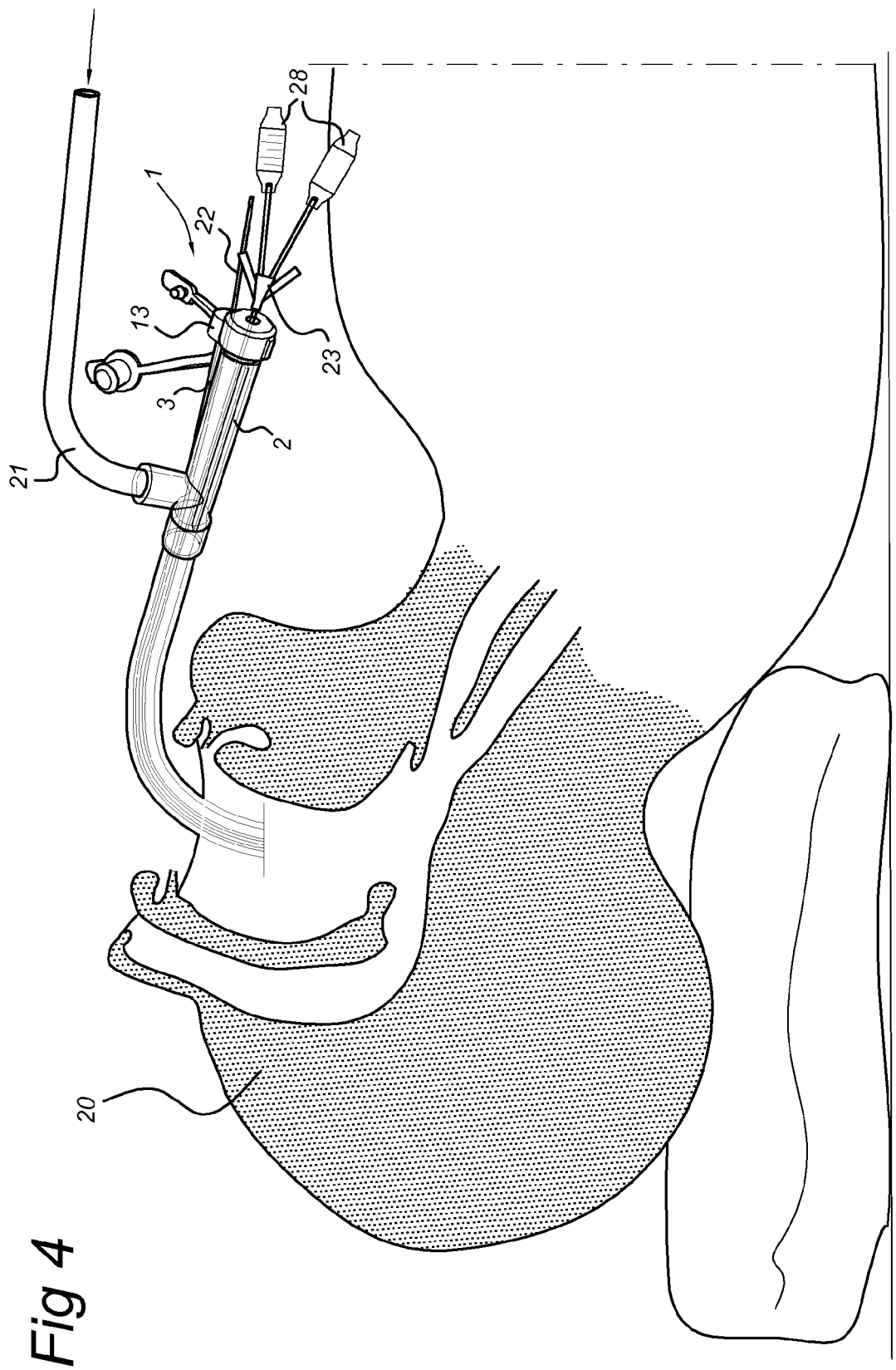
FIG. 4 shows a patient provided with a respiration tube comprising the manifold according to the present invention.

FIG. 4 shows a patient 20 provided with a respiration tube fitted with the manifold 1 according to the present invention. An air supply hose 21 is connected thereto, a bronchoscope 22 extends through the opening 16 in cap 13 of inlet 3 and a so-called blocker 23 has been introduced into the adapter via port 2.

Figure 5A:
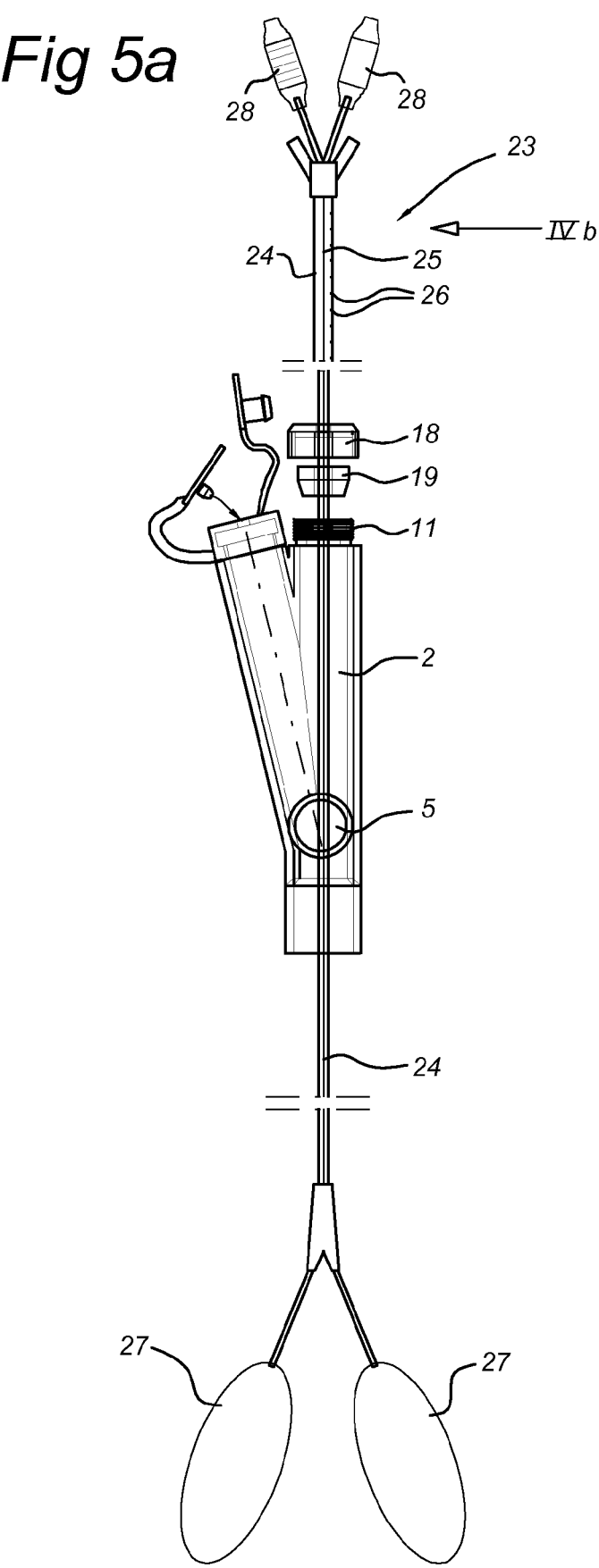
FIG. 5 shows a detail of the blocker used in FIG. 3.
Figure 5B:
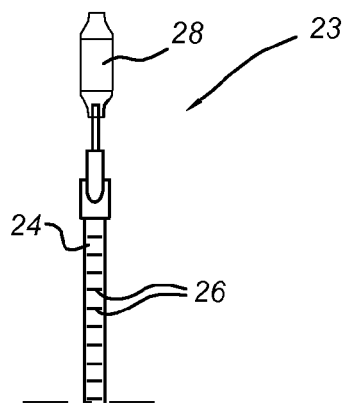

As is illustrated in FIG. 5, the blocker 23 consists of a conduit 24 to which the above-described screw cap 18 with gasket 19 is fitted which mates with screw thread 11.

At its distal end, the blocker 23 is provided with balloons 27 and when airs fed through the respective sub-part of the line 24, the balloons 27 can be inflated independently of one another.

With certain applications, it may be important for the position of the parts 27 to be determined accurately with respect to the branching of the airways.

To this end, it is important that the position of line 24 can be determined accurately with the adapter 1 according to the invention, both with regard to its length and its rotational position.

When using the blocker 23 to be described with reference to FIG. 5, it is important that both balloons are always inserted into different bronchi, and for this reason correct positioning of such a blocker at the carina is important.

According to the present invention, this is achieved by means of the line marking 26 which indicates the length and/or depth position, and a marking 25 extending in the longitudinal direction, for example a line or other indication which shows the rotational position. The marking 25 indicating the rotational position corresponds to the marking of one of the balloons 27 and/or the respective distal end. As is illustrated in FIG. 5, two air-supply connections 28 are provided to which, for example, an injection syringe acting as an air pump can be fitted. These air-supply connections 28 are connected to the balloons 27 by means of the lumen in blocker 23. Here, the air-supply connections 28 may have different colours which correspond to the colours of the differently coloured balloons 27 and/or the respective distal ends. In this case, for example, the marking 25 extends from the left-hand balloon 27 to the left-hand air-supply connection 28, so that the treating physician knows exactly which balloon he or she is operating and in which rotational position the latter is situated. The conduit 24 is preferably arranged in such a manner that the line marking 26 which indicates the length and/or depth position is situated on top of line 24. The marking 25 which indicates the rotational position is then situated on the side of line 24, that is to say at an angle of 90 degrees with respect to the horizontal conduit marking 26.

Figure 6:
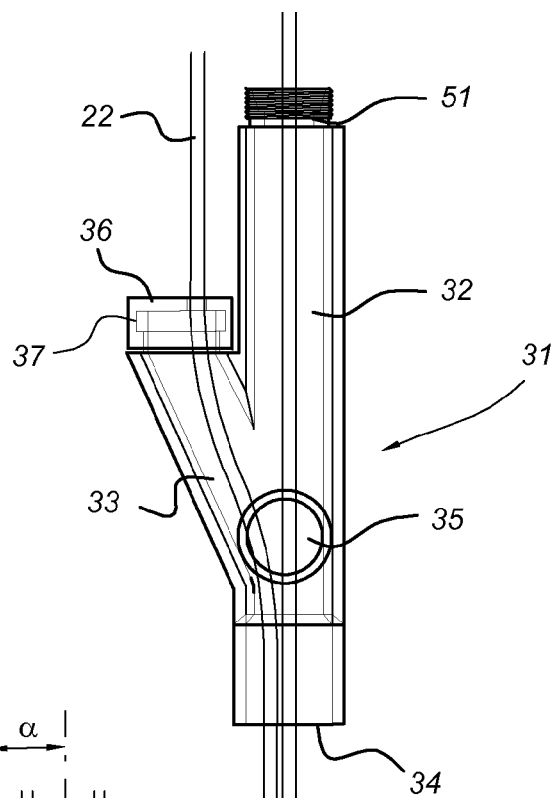
FIG. 6 shows a variant of the manifold according to the invention.

FIG. 6 shows a variant of the present invention, in which the adapter or the manifold is denoted overall by reference numeral 31. The body thereof comprises an instrument port 32 and a bronchoscope inlet 33. The exit is denoted by reference numeral 34. The entrance for the air hose is denoted by reference numeral 35. In contrast to the above-described embodiment, the bronchoscope inlet 33 is much shorter than the instrument port 32. This makes it possible to introduce the bronchoscope 22 into the adapter 31 at an angle to the port 32 which is as small as possible. On the bronchoscope inlet 33, a sealing plug 36 is permanently present which is fitted over the edge 37 by means of a click-fit. The opening provided in the sealing plug 36 can be closed by means of an ancillary plug 15 in the manner described with reference to FIG. 1 prior to/after use (of a bronchoscope). It appears that the screw thread 51 is at a considerable distance from the sealing plug 36, as a result of which a part which is to be screwed onto screw thread 51 can be fitted without obstructing sealing plug 36.

Figure 7:
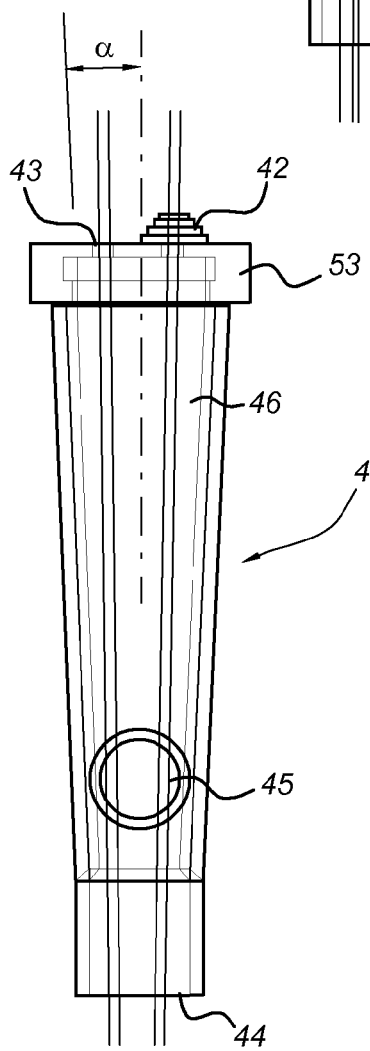
FIG. 7 shows a further variant of the manifold according to the present invention.

FIG. 7 shows a further variant of the invention which is denoted overall by reference numeral 41. The exit is denoted by reference numeral 44, while the entrance for air is denoted by reference numeral 45. In this case, the port and inlet have been combined to form a single duct at least as regards the body of the adapter. This duct 46 is fitted with a common cap 53 which is provided with a port 42 and an inlet 43 which is situated at a distance therefrom. As can be seen in FIG. 7, the port 42 is embodied as a bellows. As a result thereof, it is possible for an instrument to be introduced thereby, such as the above-described blocker, to perform axial movements while maintaining the sealing action. Closure 53 can be provided in the above-described way with closures for port 43 when it is not being used. The illustrated angle a between inlet and port which can thus be achieved can be particularly small.

With this embodiment, it is possible to move the blocker 23, and more particularly line 25 thereof, to and fro during treatment of the lungs with respect to the adapter while maintaining the sealing action between those two parts. In particular when performing operations or other actions, the lung will be moved with respect to the remainder of the body and it is desirable for the respective fitted balloon 27 to undergo the same displacement. On the other hand, it is important that the adapter remains in position as much as possible, which makes it necessary to allow the line 25 and the adapter to move with respect to one another. According to a particular aspect of the present invention, this is achieved by means of the above-described bellows 42. It will be understood that any other kind of sealing which allows the mutual axial displacement of the line 25 and the adapter can be used. Preferably, the embodiment is such that rotation between the line 25 and the adapter is noticed immediately or is even impossible. In addition, it is possible for a bellows 44 or other sealing which allows axial displacement to be provided at the exit of the adapter.

Upon reading the above, those who are skilled in the art will immediately be able to think of variants which, in light of the above, are obvious and covered by the scope of the appended claims. In addition, rights are sought for the embodiment of the blocker as such, that is to say without combination with the adapter and/or manifold according to the present invention. This relates in particular to the manner of indicating the length position and the rotational position thereof in the manner indicated above. It also relates to the provision of a sealing which permits the mutual displacement of the line of the blocker in the axial direction while maintaining the sealing action.

The invention claimed is:

1. A bronchoscopic manifold configured to be fitted to a respiration tube of a medical patient, the bronchoscopic manifold comprising:
 a gas exit port configured to effect fluid communication between the bronchoscope manifold and lungs of the medical patient via the respiration tube;
 a gas entrance port configured to supply respiratory air to the bronchoscopic manifold;
 an instrument port configured to receive an instrument, a longitudinal axis of the instrument port being substantially coaxial with a longitudinal axis of the gas exit port;
 a bronchoscope port configured to receive a bronchoscope, the bronchoscope port adjoining the instrument port;
 a cap configured to be releasably connected to the bronchoscope port, the cap comprising a plug and a sealing cap, the plug being configured to close a free end of the bronchoscope port and the sealing cap being configured to close a free end of the instrument port; and
 a confluence passage defined within the bronchoscopic manifold, the confluence passage disposed between the instrument port and the gas exit port and disposed between the bronchoscope port and the gas exit port, the instrument port being in fluid communication with the bronchoscope port and the gas entrance port via the confluence passage,
  wherein a longitudinal axis of the bronchoscope port and the longitudinal axis of the instrument port define a first plane, and a second plane is perpendicular to the first plane, and
  wherein a longitudinal axis of said gas entrance port extends at a first angle between about +45 degrees and about −45 degrees with respect to the second plane.

2. The bronchoscopic manifold according to claim 1, wherein the longitudinal axis of said gas entrance port extends substantially perpendicular to said first plane.

3. The bronchoscopic manifold according to claim 1, wherein the longitudinal axis of said bronchoscope port extends at a second angle less than 15 degrees relative to the longitudinal axis of said instrument port.

4. The bronchoscopic manifold according to claim 1, further comprising a closure disposed on a free end of the instrument port.

5. The bronchoscopic manifold according to claim 4, wherein said closure comprises a screw thread disposed on said free end and a screw cap which mates with the screw thread, the screw cap being different from the sealing cap.

6. The bronchoscopic manifold according to claim 5, wherein said screw thread is disposed on the instrument port and extends beyond the bronchoscope port along the longitudinal axis of the instrument port.

7. The bronchoscopic manifold according to claim 4, wherein the closure defines an opening configured to receive the instrument.

8. The bronchoscopic manifold according to claim 7, wherein the sealing cap is configured to be releasably inserted within the opening defined by the closure.

9. The bronchoscopic manifold according to claim 1, further comprising a proximal surface disposed opposite the gas exit port, wherein the instrument port and the bronchoscope port are disposed on the proximal surface.

10. The bronchoscopic manifold according to claim 1, further comprising a seal disposed within the bronchoscopic manifold and between the instrument port and the gas exit port, wherein the seal is configured to provide sliding sealing engagement with a conduit received by the instrument port.

11. An assembly, comprising:
the bronchoscopic manifold according to claim 1; and
an airway-blocking device having a distal end inserted through the instrument port of the bronchoscopic manifold, the airway blocking device comprising:
a conduit, and
a sealing balloon disposed on the distal end of the airway-blocking device in fluid communication with the conduit.

12. The assembly according to claim 11, wherein the distal end of the airway-blocking device includes branched ends, the sealing balloon disposed on one of the branched ends.

13. The assembly according to claim 11, further comprising markings disposed on said conduit for determining a position of the airway-blocking device relative to the bronchoscopic manifold.

14. The assembly according to claim 11, further comprising a rotational position marking disposed on said conduit.

15. A method for performing a treatment on airways of a medical patient, the method comprising:
providing the bronchoscopic manifold according to claim 1;
connecting the respiration tube to the gas exit port;
fitting said respiration tube into the airways of the medical patient;
introducing a distal end of an airway-blocking device into the airways of the medical patient via the instrument port, the gas exit port, and the respiration tube, the airway blocking device including a conduit, and a sealing balloon disposed on the distal end of the airway-blocking device in fluid communication with the conduit;
locating the sealing balloon in a desired location within the airways of the medical patient; and
inflating the sealing balloon via the conduit.

16. The bronchoscopic manifold according to claim 1, wherein the free end of the bronchoscope port comprises a click-fit edge over which the cap is configured to be releasably connected.

17. The bronchoscopic manifold according to claim 1, wherein the cap defines an opening configured to receive the bronchoscope.

18. The bronchoscopic manifold according to claim 17, wherein the plug is configured to be releasably inserted within the opening defined by the cap.

19. The bronchoscopic manifold according to claim 1, wherein the plug and sealing cap are connected to opposite sides of the cap.

* * * * *